(12) United States Patent
Childers et al.

(10) Patent No.: US 7,390,388 B2
(45) Date of Patent: Jun. 24, 2008

(54) METHOD OF SORTING CELLS ON A BIODEVICE

(75) Inventors: Winthrop D. Childers, San Diego, CA (US); David Tyvoll, La Jolla, CA (US)

(73) Assignee: Hewlett-Packard Development Company, L.P., Houston, TX (US)

(*) Notice: Subject to any disclaimer, the term of this patent is extended or adjusted under 35 U.S.C. 154(b) by 881 days.

(21) Appl. No.: 10/808,945

(22) Filed: Mar. 25, 2004

(65) Prior Publication Data

US 2005/0211556 A1    Sep. 29, 2005

(51) Int. Cl.
*G01N 27/447* (2006.01)
*G01N 27/453* (2006.01)

(52) U.S. Cl. .................. 204/547; 204/643; 204/450; 204/600

(58) Field of Classification Search .......... 204/450, 204/600, 547, 643
See application file for complete search history.

(56) References Cited

U.S. PATENT DOCUMENTS

| | | | |
|---|---|---|---|
| 4,874,507 A | 10/1989 | Whitlock | |
| 4,911,806 A | 3/1990 | Hofmann | |
| 5,126,022 A | 6/1992 | Soane et al. | |
| 5,344,535 A | 9/1994 | Betts et al. | |
| 5,375,878 A * | 12/1994 | Ellerbrok | 280/743.1 |
| 5,427,663 A * | 6/1995 | Austin et al. | 204/549 |
| 5,454,472 A | 10/1995 | Benecke et al. | |
| 5,589,047 A | 12/1996 | Coster et al. | |
| 5,626,734 A | 5/1997 | Docoslis et al. | |
| 5,653,859 A | 8/1997 | Parton et al. | |
| 5,814,200 A | 9/1998 | Pethig et al. | |
| 5,858,192 A | 1/1999 | Becker et al. | |
| 5,938,904 A | 8/1999 | Bader et al. | |
| 5,993,630 A | 11/1999 | Becker et al. | |
| 5,993,631 A | 11/1999 | Parton et al. | |
| 6,056,861 A | 5/2000 | Fuhr et al. | |
| 6,059,950 A | 5/2000 | Dames et al. | |
| 6,149,789 A | 11/2000 | Benecke et al. | |
| 6,193,866 B1 | 2/2001 | Bader et al. | |
| 6,197,176 B1 | 3/2001 | Pethig et al. | |
| 6,264,815 B1 | 7/2001 | Pethig et al. | |
| 6,287,832 B1 | 9/2001 | Becker et al. | |
| 6,306,272 B1 | 10/2001 | Soane et al. | |
| 6,310,309 B1 | 10/2001 | Ager et al. | |

(Continued)

FOREIGN PATENT DOCUMENTS

WO    WO 97/34689    9/1997

(Continued)

OTHER PUBLICATIONS

Miller et al. (Electro-orientation of ellipsoidal erythrocytes- Theory and experiment, Biophys. J. vol. 64, May 1993, pp. 1588-1595).*

(Continued)

*Primary Examiner*—Alex Noguerola (57) ABSTRACT

A method of sorting cells for a biodevice comprises directing a flow of cells within a fluid into a filtration structure defining an array of fluid openings and encouraging cell passage of each cell of a portion of the cells through the fluid openings based on at least one dimension of each cell via application of an electric field within the fluid openings.

25 Claims, 5 Drawing Sheets

U.S. PATENT DOCUMENTS

| | | | |
|---|---|---|---|
| 6,403,367 | B1 | 6/2002 | Cheng et al. |
| 6,465,225 | B1 | 10/2002 | Fuhr et al. |
| 6,537,433 | B1 | 3/2003 | Bryning et al. |
| 6,540,895 | B1 | 4/2003 | Spence et al. |
| 6,596,143 | B1 | 7/2003 | Wang et al. |
| 6,610,188 | B1 | 8/2003 | Fuhr et al. |
| 6,641,708 | B1 | 11/2003 | Becker et al. |
| 6,660,493 | B2 | 12/2003 | Miles |
| 6,673,225 | B1 | 1/2004 | Arnold |
| 6,685,810 | B2 * | 2/2004 | Noca et al. ............ 204/450 |
| 6,685,812 | B2 | 2/2004 | Miles |
| 6,727,451 | B1 | 4/2004 | Fuhr et al. |
| 6,730,204 | B2 | 5/2004 | Mariella, Jr. |
| 6,749,736 | B1 | 6/2004 | Fuhr et al. |
| 6,761,811 | B2 | 7/2004 | Mariella, Jr. |
| 7,135,144 | B2 * | 11/2006 | Christel et al. ............ 422/99 |
| 7,150,812 | B2 * | 12/2006 | Huang et al. ............ 204/451 |
| 2002/0005354 | A1 | 1/2002 | Spence et al. |
| 2002/0036141 | A1 | 3/2002 | Gascoyne et al. |
| 2002/0042125 | A1 | 4/2002 | Peterson et al. |
| 2002/0055167 | A1 | 5/2002 | Pourahmadi et al. |
| 2002/0076825 | A1 | 6/2002 | Cheng et al. |
| 2002/0182627 | A1 | 12/2002 | Wang et al. |
| 2002/0182654 | A1 | 12/2002 | Jing et al. |
| 2003/0010637 | A1 | 1/2003 | Cummings |
| 2003/0121788 | A1 | 7/2003 | Gascoyne et al. |
| 2003/0134416 | A1 | 7/2003 | Yamanishi et al. |
| 2003/0159932 | A1 | 8/2003 | Betts et al. |
| 2004/0011652 | A1 | 1/2004 | Bressler |
| 2005/0042766 | A1 * | 2/2005 | Ohman et al. ............ 436/174 |

FOREIGN PATENT DOCUMENTS

| | | |
|---|---|---|
| WO | WO 98/10869 | 3/1998 |
| WO | WO 02/12896 | 2/2002 |
| WO | WO 02/28523 | 4/2002 |
| WO | WO 03/014291 | 2/2003 |
| WO | WO 03/093496 | 11/2003 |

OTHER PUBLICATIONS

Gimsa ("A comprehensive approach to electro-orientation, electrodeformation, dielectrophoresis, and electrorotation of ellipsoidal particles and biological cells," Bioelectrochemistry 54 (2110) 23-31).*

Tsuda, Takao, Yamauchi, Norihiro, and Kitagawa, Shinya, "Separation of Red Blood Cells at the Single Cell Level by Capillary Zone Electrophoresis", Analytical Sciences, vol. 16, pp. 847-850, (Aug. 2000).

Holmes, David and Morgan, Hywel, "Cell Positioning and Sorting Using Dielectrophoresis", European Cells and Materials, vol. 4, Suppl. 2, pp. 120-122, (2000).

Swiss Center for Electronics and Microtechnology, "Dielectrophoretic Size-Sensitive Particle Filter for Micro-Fluidic Applications", 2 pgs., printed Feb. 24, 2004 from www.csem.ch/corporate/Report2002/pdf/microrobotics.pdf.

* cited by examiner

METHOD OF SORTING CELLS ON A BIODEVICE

CROSS-REFERENCE TO RELATED APPLICATIONS

This application is related to U.S. patent application Ser. No. 10/808,803, entitled "METHOD OF SORTING CELLS IN SERIES", and U.S. patent application Ser. No. 10/808,987, entitled "CELL TRANSPORTER FOR A BIODEVICE", both filed on Mar. 25, 2004, and incorporated herein by reference.

BACKGROUND

The rapid miniaturization in electronic devices, particularly their manufacture and assembly, has transformed the medical industry. In particular, handling and testing of cells and other components within body fluids has moved beyond the conventional test tube to other devices, such as biochips. A biochip, sometimes called a lab-on-a-chip, refers to the placement of testing of biologic materials on a miniature electronic device capable of electrically and/or chemically interacting with the biologic materials.

Considerable efforts have been made in the biochip environment to apply electric fields to manipulate cells, including their movement, separation, property determination, etc. Despite numerous attempts at cell manipulation with electric fields, the ability to manipulate cells is still limited by different characteristics of the cells, such as cell size, cell aggregation, cell polarizability, etc. For example, sorting cells into different groups is challenged by the great variety of sizes, shapes, polarizability, relative volumes of cells within a fluid, etc. Cell sorting is also affected by the characteristics of the fluid in which the cells are suspended during manipulation. Impeding sorting of the cells on the biochip, in turn, hampers the ability to perform other functions with the cells (e.g., collection, isolation, testing, etc.) on the biochip.

For these reasons, among others, widespread use of biochip devices has been limited.

DETAILED DESCRIPTION

In the following detailed description, reference is made to the accompanying drawings which form a part hereof, and in which is shown by way of illustration specific embodiments in which the invention may be practiced. In this regard, directional terminology, such as "top," "bottom," "front," "back," "leading," "trailing," etc., is used with reference to the orientation of the Figure(s) being described. Because components of embodiments of the present invention can be positioned in a number of different orientations, the directional terminology is used for purposes of illustration and is in no way limiting. It is to be understood that other embodiments may be utilized and structural or logical changes may be made without departing from the scope of the present invention. Finally, although a flow chart in the figures of this application shows a specific order of execution, the order of execution may differ from that which is depicted. The following detailed description, therefore, is not to be taken in a limiting sense, and the scope of the present invention is defined by the appended claims.

Embodiments of the present invention are directed to a method for sorting cells on a biodevice by enhancing cell discrimination based on a dimensional orientation of the cells and/or a size of the cells. In one embodiment, this biodevice is a miniature stand-alone electronic device (such as a biochip) used for performing operations on biologic materials, such as separating and/or testing cells, and includes a mechanism for sorting cells for collection, discard, and/or testing.

In one embodiment, a size-based sorter of the biodevice comprises one or more fluid barrier structures defining one or more arrays of openings that discriminately permit passage of cells based on their size. In particular, the cells are moved within a fluid flow path in a first direction through a succession of arrays of fluid flow openings with each array of fluid flow openings permitting passage of a different sized cell. In some embodiments, each successive array of openings permits passage of cells that have a smaller size than the previous array of openings. The space between successive arrays also defines a set of independent passageways for moving cells, via a temporally varying non-uniform electric field (e.g., a traveling wave dielectrophoretic field) applied by an electrode arrangement, in a second direction away from the arrays of openings. In particular, cells which can no longer pass through the next array of openings in the succession of arrays are temporarily collected in the respective passageway, and are thereby grouped by size for transport away from the openings via the temporally varying non-uniform electric field, such as a traveling wave dielectrophoretic field (described in more detail below).

In one embodiment, each fluid barrier structure is an array of individual barriers that cooperate to form the arrays of openings or passages. More specifically the openings are actually gaps or spacings between the individual fluid barriers. Other ways of forming arrays of openings are possible, however, such as forming a monolithic structure such as a micro-machined sheet that defines the openings as passages through the structure.

In one embodiment, a dimension-orientation sorter of the biodevice comprises one or more arrays of openings in combination with an alignment mechanism such as an electric field to discriminately permit passage of cells based upon the dimension and alignment of each individual cell. In particular, gap-passable cells are oriented by the alignment mechanism for passage through the arrays of openings while non-passable cells are prevented from passing through the openings based upon their dimensions and/or inability to properly orient to the openings.

In one embodiment, the alignment mechanism and array of openings of the dimension-orientation sorter act to discriminate cells based on their dimensions along two axes. In this embodiment, the passable cells tend to have at least one major axis. Examples of passable cells include those cells having prolate or cigar shapes (e.g., having one major axis), oblate shapes (e.g., having two major axes), or more generally ellipsoidal shapes (e.g., having a major axis, an intermediate axis, and a minor axis). An example of cells having two major axes are red blood cells having an approximately oblate shape.

In another embodiment, the gap-passable cells (i.e., cells to be passed through the openings) are prolate or cigar shaped with each cell having one major axis and two minor axes. The non-passable cells (i.e., cells not to be passed through the openings) in this example have a geometry approaching a generally spherical shape. The passable cells pass through the openings in a direction of travel through the barrier structure. The openings each have dimensions perpendicular to the direction of travel that are greater than the minor axes of the passable cells. To facilitate proper alignment, the electric field aligns the major axis of each passable cell to the direction of travel.

In another embodiment, the gap-passable cells are red blood cells with each red blood cell having two major axes and a minor axis. The non-passable cells have each of their three axes larger than the minor axis of the red blood cells. The red blood cells pass through the openings defined by the barrier structure in a direction of travel or fluid flow. Each of the openings has an elongate cross section perpendicular to the direction of travel of the cells and define a major axis that is larger than the major axis of the red blood cells and a minor axis that is greater than the minor axis of the red blood cells. To facilitate proper passage of the red blood cells through the openings, an electric field is applied to align the red blood cells such that at least one major axis of each red blood cell is induced to align with at least the major axis of each opening. In some embodiments, the second major axis of each red blood cell also is also induced to align with the direction of travel.

In another embodiment, the passable cells each have a major axis, a minor axis, and an intermediate axis. Each opening has an elongate shape having a major axis that is greater in extent than the intermediate axis of each passable cell and a minor axis that is greater in extent than the minor axis of each passable cell. In this example, the electric field preferably aligns the passable cells such that the long axis of each cell is in the direction of travel and the intermediate axis of each cell is aligned with the major axis of each opening. This arrangement would maximize sorting efficiency, but even partially aligning one of the two axes of the passable cells would provide some increase in sorting efficiency.

In some embodiments, one or more dimension-orientation sorter(s) and one or more size-based sorters can be combined in series. In one embodiment, a size-based sorter precedes a dimension-orientation sorter while in other embodiments, a size-based sorter precedes a dimension-orientation sorter.

In some embodiments, the electrode arrangement of the biodevice moves cells during and/or after sorting by application of a traveling wave dielectrophoretic field that induces cell motion within a suspending fluid. This dielectrophoretic field is applied via one or more electrode arrays disposed on the biodevice within or adjacent the dimension-orientation sorter and/or size-based sorter, and is described in more detail below.

In one embodiment, a dielectrophoretic field can be applied by the biodevice to align cells in a dimension-orientation sorter and/or to move size-sorted cells in a size-based sorter. This dielectrophoretic field can be defined as an electric field that varies spatially or is non-uniform where it is being applied to the particles (e.g. cells). Positive dielectrophoresis occurs when the particle (e.g. cell) is more polarizable than the medium (e.g., buffer solution) and results in the particle being drawn toward a region of higher field strength. A system operating in this way can be referred to as operating in a positive dielectrophoresis mode. Negative dielectrophoresis occurs when the particle is less polarizable than the medium and results in the particle being drawn toward a region of lesser field strength. A system operating in this way can be referred to as operating in a negative dielectrophoresis mode.

First, these electric fields are generated by applying a voltage between two or more electrodes. The field electrodes are disposed and arranged in a geometric relationship relative to one another to cause a non-uniformity or spatial variation in the applied electric field, which produces the dielectrophoretic effect. Accordingly, selectively applied variations in this geometric relationship of the field electrodes are used to cause desired movements of cells within the dielectrophoretic fields.

Second, by applying a time varying voltage to the field electrodes, a temporally varying electric field can be produced. This time variation will tend to affect the polarization of the fluid medium and the particles differently—hence it will affect the relative polarization between the fluid medium and the particles. Accordingly, selective application of time variance in the dielectophoretic field can be used to move cell particles in a desired manner.

In many cases, particularly where the variation is sinusoidal, the time variation has a characteristic frequency. The relative polarization of a particle relative to the medium is typically affected by the applied frequency. Large changes in frequency can be sufficient to change a system from operating in a negative dielectrophoresis mode to a positive dielectrophoresis mode. For example, there may be one frequency wherein the cells move toward regions of higher field strength (the positive dielectrophoresis mode) and another frequency wherein the cells move away from regions of higher field strength (the negative dielectrophoresis mode). Either negative or positive dielectrophoresis may be used in the embodiments of the present invention to move cells within a fluid medium.

Third, when using more than two field electrodes, certain types of motion can be induced by selectively shifting which pair of electrodes has a voltage difference or using an amplitude modulation technique. For example, an arrangement of four interleaved and independent field electrodes can induce a "traveling wave dielectrophoresis" response in the particles to allow controlled translation of the particles. This "traveling wave" effect is used impart motion for transporting cells or particles through a passageway of a biodevice.

In one embodiment, the operation of the electrode arrangement in a dimension-orientation sorter and/or size-based sorter is controlled by a controller associated with the respective sorters to achieve cell alignment, cell transport, etc. during cell sorting by size and/or dimensional orientation.

Figure 1:
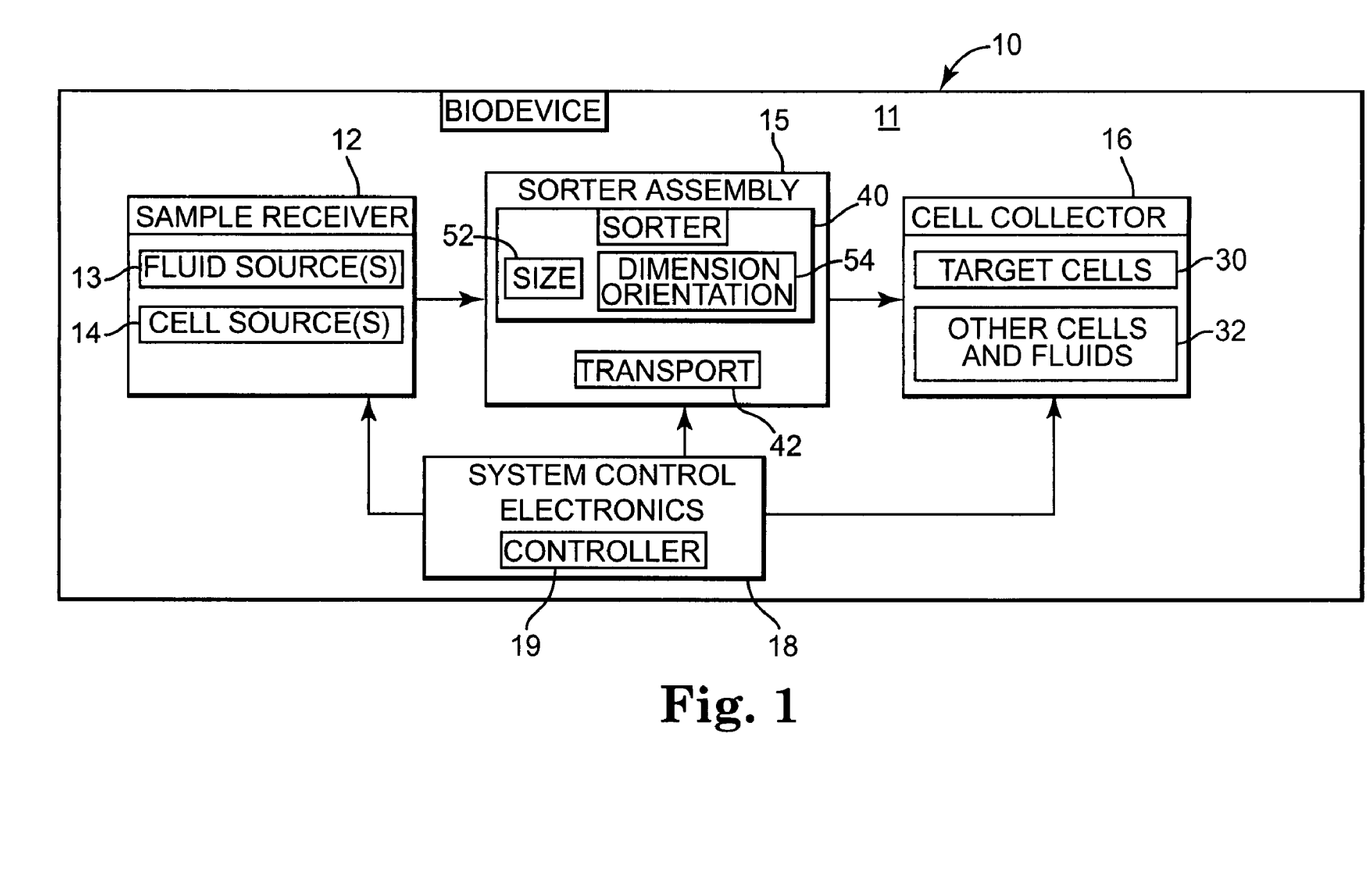
FIG. 1 is a block diagram of a biodevice, according to an embodiment of the present invention.

In one embodiment shown in FIG. 1, biodevice 10 is directed to receiving a sample of cells within a fluid, transporting and sorting the cells, and then collecting the cells as target cells and other cells (e.g., non-target cells).

As shown in FIG. 1, biodevice 10 comprises sample receiver 12, sorter assembly 15, cell collector 16, and system control electronics 18 with controller 19. Sorter assembly 15 comprises sorting mechanism 40 and transporter 42. Sorting mechanism 40 of sorter assembly 15 comprises size-based sorter 52 and dimension-orientation sorter 54. Cell collector 16 collects target cells 30 and other cells 32 (e.g. non-target cells) as a result of the operation of sorter assembly 15 on a fluid/cell sample from sample receiver 12.

System control electronics 18 of biodevice 10 is in electrical communication with sample receiver 12, sorter assembly 15, and cell collector 16. System control electronics 18 directs various functions of biodevice 10 including operation of controller 19 which is configured to direct various electric, acoustic, ultrasonic fields/forces to be applied by sorter 40 and/or transporter 42. In one embodiment, as further described in association with FIG. 2, controller 19 comprises a waveform generator that enables alternating current waveforms that are operable at selectable magnitudes (e.g., voltages), frequencies, phases, and polarities (e.g., negative or positive frequencies). In some embodiments, this waveform generator is capable of generating signal frequencies in the range from DC to several GHz.

Sample receiver 12 of biodevice 10 comprises fluid source(s) 13 and cell source(s) 14. Fluid source(s) 13 receive one or more types of fluid and/or fluid mediums for use on biodevice 10 while cell source(s) 14 receive one or more types of cells suitable for handling and testing on biodevice 10. Fluid source(s) 13 of biodevice 10 include, but are not limited to, one or more sources of fluid mediums, such as fluid suspensions, blood and blood derivatives (e.g., whole blood, plasma, diluted blood, etc), reagent solutions, etc. Cell source(s) 14 within biodevice 10 include, but are not limited to, one or more sources of cells, such as human cells, animal cells, etc, as well as other particles, such as cell organelles, analytes, bacteria, viruses, etc, including combinations of the same. Human cells also include, but are not limited to, blood cells such as white blood cells, red blood cells, fetal cells, nucleated or non-nucleated cells, etc. In particular, cells provided by cell source(s) 14 include cells of different sizes, shapes, and/or polarizability to enable sorting these cells according to their size and/or dimensional geometry (one or more dimensions).

Transporter 42 of sorter assembly 15 comprises a fluid flow pressure arrangement or electrode arrangement suitable for causing flowing movement of cells between different functions (e.g., testing, collecting, sorting, etc.) on biodevice 10.

Size-based sorter 52 of sorting mechanism 40 comprises one or more barrier structures defining one or more array(s) of openings interposed within a fluid flow path to discriminately permit passage of cells through the openings based on the size of the cells. This size-based sorter 52 also comprises an electrode arrangement disposed between different arrays of openings to move cells that have passed through the openings away from openings. Successive sets of openings are arranged with each array of openings having at least one dimension that is progressively changing, so that as the suspending fluid and cells flow through the arrays of openings, the cells are sorted into different groups based on their size. The electrode arrangement extends laterally (e.g., transverse to the fluid flow path) between successive barrier arrays for applying a traveling wave dielectrophoretic field to move the cells out of the way of the barriers. Size-based sorter 52 is later described in more detail in association with FIGS. 2 and 4.

Dimension-orientation sorter 54 of sorting mechanism 40 comprises one or more barrier structures interposed within a fluid flow path to discriminately permit passage of cells through openings formed in the barrier structures based primarily on the orientation of one or more dimensions of the cells. Sorter 54 is applicable for sorting cells wherein a passable portion of the cells have at least one major axis or at least one axis of elongation. This dimension-orientation sorter 54 also comprises an electrode arrangement disposed about the openings to align the major axis of each of the passable portion of the cells relative to the openings to facilitate passing of through the openings.

In one embodiment, each of the passable cells has a prolate shape (e.g., cigar shape) with a long axis that is aligned with a dipole moment. In this embodiment, dimension-orientation sorter 54 includes an electrode arrangement for aligning the long or major axis of the cells with the direction in which the cells pass through the openings. The openings in this case may be substantially circular or oval with dimensions larger than the minor axes of the passable cells.

In another embodiment, each of the passable cells has an oblate shape (e.g., flattened shape) with a single minor axis and two major axes. One example of a cell having an oblate shape is a red blood cell. Each of the openings has an elongate shape with a major axis that exceeds the dimension of the major axis of each passable cell and a minor axis that exceeds the minor axis of each passable cell. The electrode arrangement is disposed to at least align one major axis of the passable cells with the major axis of the openings.

Accordingly, dimension-orientation sorter 54 enables passage of cells that are responsive to electric fields (e.g., uniform or non-uniform electric fields) so that upon alignment of the cells with the electric field, the cells are aligned for passage through the openings. Cells that are not responsive the electric field, and/or that lack a dimensional configuration that is passable through the openings with the alignment, do not pass through the dimension-orientation sorter 54.

In some embodiments, dimension-orientation sorter 54 and/or size-based sorter 52 are operated so that target cells are allowed to pass through barrier(s) of each respective sorter 52, 54 while non-target cells are excluded from passage through the barrier(s) of each respective sorter 52, 54. Accordingly, in this embodiment, sorters 52, 54 are used to remove target cells from a population of cells in the fluid flow path.

In other embodiments, dimension-orientation sorter 54 and/or size-based sorter 52 are operated so that non-target cells are allowed to pass through barrier(s) of each respective sorter 52, 54 while target cells are excluded from passage through the barrier(s) of each respective sorter 52, 54. Accordingly, in this embodiment, sorters 52, 54 are used to remove non-target cells from a population of cells in the fluid flow path.

Both size-based sorter 52 and dimension-orientation sorter 54 are described in further detail in association with FIGS. 2-9.

Figure 2:
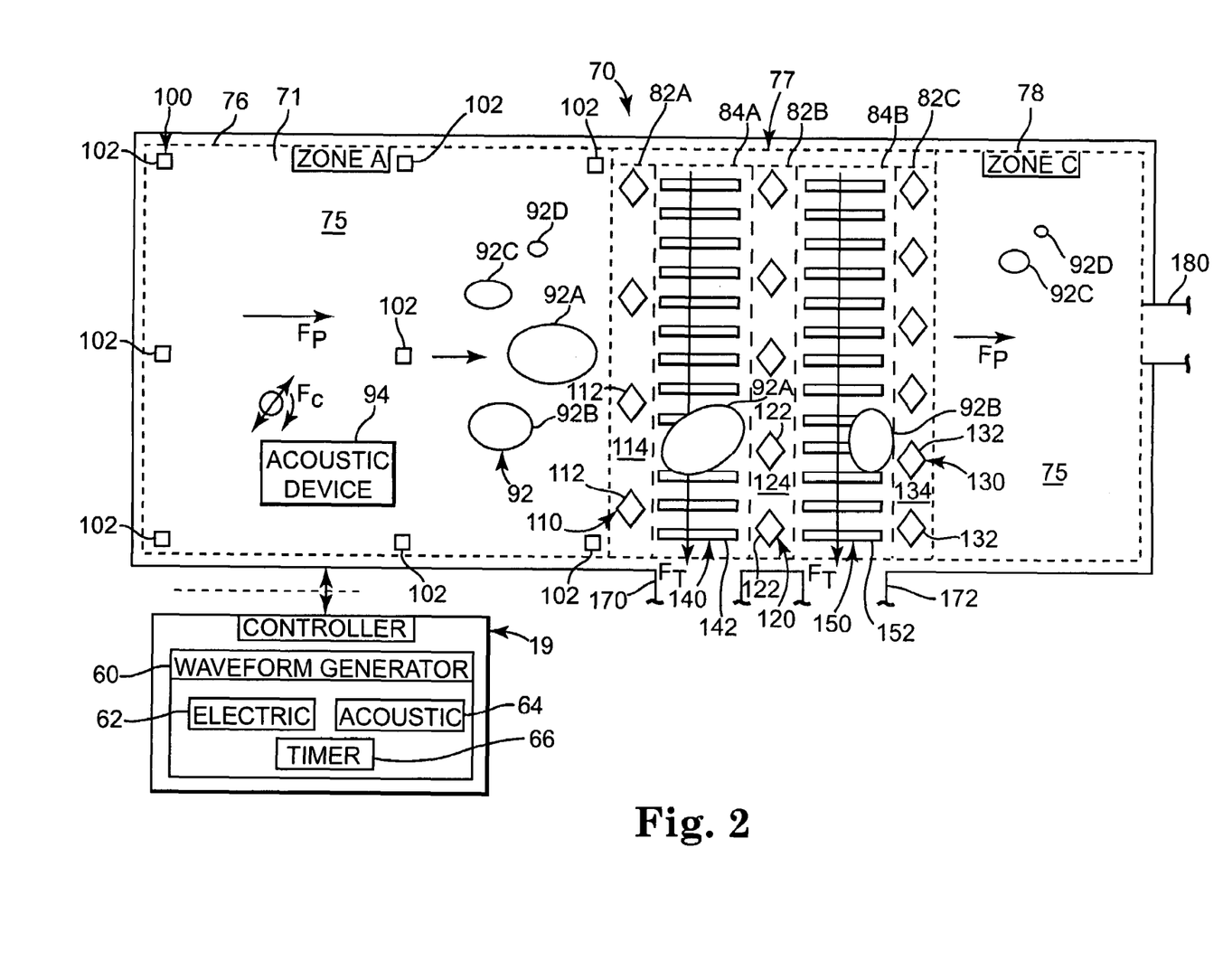
FIG. 2 is a schematic illustration of a cell sorter of a biodevice with partial plan views and block diagrams, according to an embodiment of the present invention.

FIG. 2 illustrates sorter 70, which is one embodiment of size-based sorter 52 of sorting mechanism 40 of FIG. 1. As shown in FIG. 2, size-based sorter 70 comprises surface 71, fluid 75, and three working zones including first zone 76, second zone 77 and third zone 78. Second zone 77 includes five subzones including first subzone 82A, second subzone 82B, and third subzone 82C, fourth subzone 84A, fifth subzone 84B.

The embodiment depicted in FIG. 2 uses arrays of fluid barriers to define arrays of openings or gaps between adjacent pairs of barriers.

As shown in first zone 76, fluid 75 supports a flow of cells 92 across surface 71 by a fluid flow pressure drop (represented by directional force arrow $F_P$), which pushes cells 92 toward and through second zone 77 and third zone 78. Cells 92 include first cell(s) 92A, second cell(s) 92B, third cell(s) 92C, and fourth cell(s) 92D, each of which represent different sized cells within a plurality of cells 92. The plurality of cells 92 includes a greater number of each size of cell than that shown, which has been limited for illustrative purposes. In addition, there can be more sizes or less sizes of cells than the four different sizes of cells shown. Differently-sized cells 92A, 92B, 92C, 92D are intercepted in the fluid flow by barriers within zone 77 for sorting cells 92 according to their respective sizes.

In some embodiments, cells within one or more zones 76, 77, 78 are discouraged from aggregating together to thereby enhance their sorting by size and/or dimensional orientation. In one embodiment, acoustic device 94 is disposed within first zone 76 for introducing a secondary motion such as a vibratory motion (represented by directional force arrow Fc) to prevent cells 92 from aggregating together during passage through zone 76. In other embodiments, acoustic device 94 is sized and positioned as one or more elements to also provide an anti-aggregation force on cells 92 within second zone 77 and/or third zone 78, thereby maintaining substantially free movement of individual cells 92 relative to each other as they move through size-based sorter 70.

In other embodiments, discouraging aggregation of cells 92 as they move through size-based sorter 70 is achieved by an electrorotation grid 100 disposed within zone 76, zone 77, and/or zone 78. Electrorotation grid 100 comprises an array of electrode elements 102 which are sized and spaced relative to each other to induce an electro-rotative force (via application of a phase-shifting dielectrophoretic field) on cells 92 to prevent unwanted aggregation of cells 92 relative to each other as they travel through fluid flow path of size-based sorter 70.

In some embodiments, electrorotation grid 100 and acoustic device 94 are both deployed on size-based sorter 70 either together or separately in one or more workings zones 76, 77, 78.

One mechanism for discouraging aggregation of cells during transport on a biodevice is described in detail in assignee's above-incorporated application, entitled "Cell Transporter For A Biodevice".

As shown in the embodiment of FIG. 2, second zone 77 of sorter 70 comprises one or more arrays of differently-sized passageways for discriminately permitting movement of cells based primarily on the size of each cell. Multiple arrays 110, 120, 130 of barriers define the passageways through which cells 92 flow under fluid pressure. These passageways are arranged with subzones 82A, 82B, 82C, 84A, and 84B of second zone 77, which define the area of filtration. Each of the elements of second zone 77 are formed within a substrate or can be individual elements formed onto or attached to a substrate.

A first array 110 of fluid barriers 112 is disposed within first subzone 82A and defines openings or gaps 114 through which various cells 92 can pass, such as first-sized cell(s) 92A. A second array 120 of fluid barriers 122 is disposed within second subzone 82B and defines gaps 124 through which various cells 92 can pass, such as second-sized cell(s) 92B. A third array 130 of fluid barriers 132 is disposed within third subzone 82C and defines gaps 134 through which various cells 92 can pass, such as third-sized cell(s) 92C and fourth-sized cells 92D. As shown in FIG. 2, gaps 114 are larger than gaps 124, which in turn are larger than gaps 134. In this way, barriers arrays 110, 120, 130 provide a succession of cell passageways that decrease in size as cells move through the fluid flow path.

Each of the fluid barriers 112, 122, 132 are sized and shaped to define openings or gaps 114, 124, 134, respectively. In one embodiment, as shown in FIG. 2, fluid barriers 112, 122, 132 have a diamond shape as seen from a top plan view. However, in some embodiments, fluid-barriers 112, 122, 132 have other shapes (as seen from a top plan view) such as circular, square, elliptical, triangular, etc. Moreover, in other embodiments, the fluid barriers (e.g. barrier 112) within one of the arrays (e.g., barrier array 110) can have a shape different than the shape of the fluid barriers within another of the other arrays (e.g., barrier arrays 120, 130). Finally, the barriers (e.g., barrier 112) within a single barrier array (e.g., barrier array 110) can have different shapes so that not every barrier within that array has the same shape.

In some embodiments, fluid barriers 112, 122, 132 are non-conductive and thereby do not attract cells 92 or repel cells 92 with electric fields. In other words, fluid barriers 112, 122, 132 are not electrically active in sorting cells according to their sizes. Rather, fluid barriers 112, 122, 132 encourage discrimination among different sized cells based only on the geometric shape of the barriers and the positioning of the barriers relative to one another.

As also shown in the embodiment of FIG. 2, subzone 84A of zone 77 defines an area between barrier array 110 and barrier array 120 in which electrode array 140 of elements 142 is disposed. In particular, subzone 84A defines a passage through which cells 92A are pushed in a second direction by a traveling wave dielectrophoretic field (applied by electrode array 140 and represented by $F_T$) after moving through gaps 112 under fluid pressure in the first direction. Similarly, subzone 84B of zone 77 defines an area between barrier array 120 and barrier array 130 in which electrode array 150 of elements 152 is disposed. In particular, subzone 84B defines a passageway through which cells 92B are pushed in the second direction by a traveling wave dielectrophoretic field (applied by electrode array 150 and represented by $F_T$) after moving through gaps 124 under fluid pressure in the first direction.

In some embodiments, elements 142 of electrode array 140 and/or elements 152 of electrode array 150 are arranged in an interleaved or interdigitated pattern. In some embodiments, electrode arrays 140, 150 are exposed on surface 71 of a substrate defining sorter 70, while in other embodiments, electrode arrays 140, 150 are disposed just below surface 71 of the substrate defining sorter 70.

Electrode array(s) 140, 150 are configured to apply the previously described dielectrophoretic field as a traveling wave to move these cells or particles along substantially the whole length of the passageways defined by subzones 84A, 84B. In one embodiment, electrode arrays 140, 150 are used to achieve this traveling wave effect by linking every fourth electrode element together to form a signal channel (e.g., channel A) to permit activating and deactivating those linked elements together as a single unit. By repeating this arrangement, all of the electrode elements 142 or 152 of arrays 140, 150 respectively, are distributed into four operational sets in which each set defines a channel to enable four distinct signal channels (e.g., channels A, B, C, D) to be applied to electrode array 140, 150 for implementing independent driving of each of the four operational sets. In this manner, electrode array(s) 140, 150 enable application of a traveling wave in a spatially varying electric field to move cell(s) 92A through the passageway of subzone 84A between the respective barrier array 110 and 120 and to move cells 92B through the passageway of subzone 84B between respective barrier arrays 120 and 130.

Third zone 78 of size-based sorter 70 defines an area beyond the barrier arrays 110, 120, 130 of second zone 77 in which cells 92C, 92D arrive by fluid flow pressure after passing through gaps 114, 124, and 134 respectively.

Accordingly, cells of different sizes are sorted into different groups according to their size by barrier arrays 110, 120, 130 and then are moved out of the way in groups independently from each other by traveling waves according to each size-grouping. Each group of size-sorted cells is separately pushed out of the zones 84A, 84B through ports 170, 172 respectively. Cells, such as cells 92C, 92D, that are not filtered out of the stream of cells, pass by traveling wave zones 84A, 84B to third zone 78 for further manipulations, collections, or exiting via port 180.

In one embodiment, more than three barrier arrays can be arranged in sequence for consecutive sorting by size. For each additional passageway created by additional barrier arrays, an electrode array substantially similar to electrode arrays 140, 150 is disposed between each barrier array to move cells.

As also shown in the embodiment of FIG. 2, controller 19 of system control electronics 18 (FIG. 1) comprises waveform generator 60 having electric field control module 62, acoustic control module 64, and timer 66. Electric control module 62 of waveform generator 60 is configured to generate a waveform suited for inducing electric fields that are uniform or non-uniform (e.g., dielectrophoretic fields, with or without a traveling wave), for aligning, rotating, and/or linearly transporting cells. For example, electric control module 62 can control electrorotation grid 100 and/or traveling wave electrode arrays 140, 150. Acoustic control module 64 controls acoustic device 94 to generate physical fields for inducing motion(s) in cells 92 that counteract aggregation of cells prior to and/or during sorting. Controller 19 also comprises timer 66, which enables selective activation and deactivation of electric field control module 62 and acoustic module 64 so that modules 62, 64 can operate simultaneously or alternately relative to each other.

Accordingly, sorter 70 in combination with controller 19 operate to sort cells into different groups according to their size (via barrier arrays 110, 120, 130) and then move the groups of size-sorted cells out of the sorter in generally parallel, independent pathways (e.g., subzones 84A, 84B) to maintain separation of the groups of cells.

Figure 3:
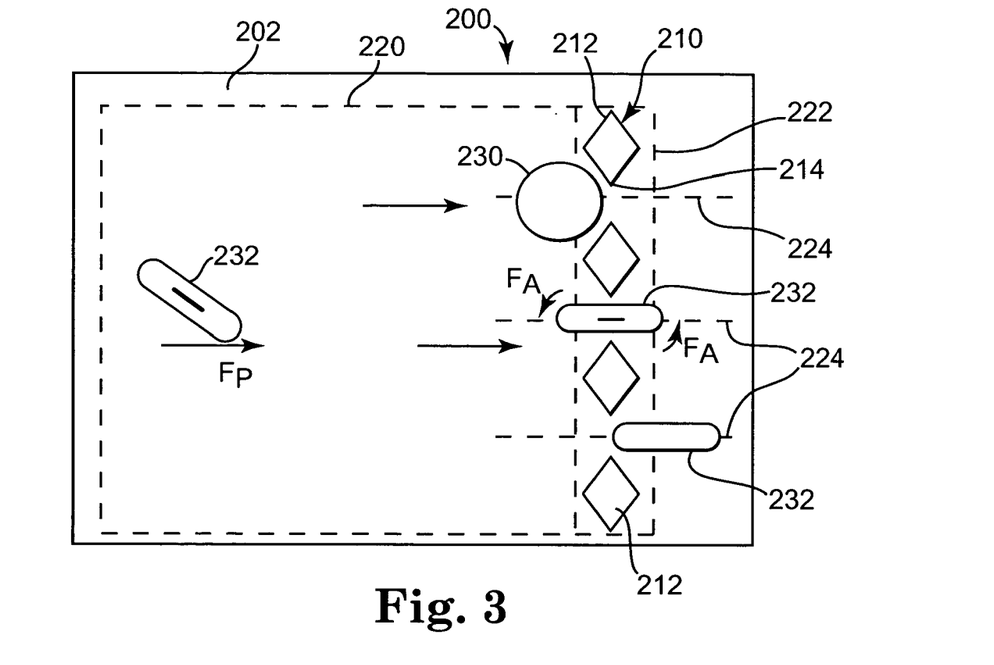
FIG. 3 is plan view schematically depicting another cell sorter, according to an embodiment of the present invention.

FIG. 3 is a plan view of a dimension-orientation sorter 200 which is an embodiment of dimension-orientation sorter 54 of FIG. 1. Dimension-orientation sorter 200 sorts cells by electrically orienting appropriately-shaped, electrically-responsive cells for passage through an array of openings. In the embodiment depicted in FIG. 3, the array of openings is defined by an array of fluid flow barriers. Gaps between adjacent fluid flow barriers define openings.

As shown in the embodiment of FIG. 3, dimension-orientation sorter 200 comprises surface 202 and array 210 of fluid flow barriers 212 that define gaps 214. Sorter 200 defines first zone 220 and second zone 222, and is operated via controller 19 including electric field control module 62 (FIG. 2).

First zone 220 of sorter 200 defines a pre-sorting area in which non-passable cell(s) 230 and gap-passable cell(s) 232 move toward barrier array 210 under a fluid flow pressure (indicated by directional arrow $F_P$). Non-passable cell(s) 230 define one or more cells that have one or more dimensions and/or conductive properties which prevent passage of the non-passable cell(s) 230 through gaps 214. In some embodiments, non-passable cells include cells having a spherical shape with a diameter greater than the width of the gaps. In some embodiments, gap-passable cell(s) 232 define one or more cells that have both a responsive conductive property (i.e., the cell aligns its axes to an electric field) and a shape with one or more dimensions capable of passing through gaps 214 when cell(s) 232 are properly oriented to gaps 214. Each gap-passable cell 232 has a length and/or a width that is generally no greater than a width of gaps 214. Examples of suitable gap-passable cells 232 include cells having an oblate shape, a prolate shape, a generally cylindrical shape, etc.

Second zone 222 of sorter 200 defines an area adjacent to barrier array 210 in which an electric field is applied to which dipole elements, such as cells, are responsive. Based on the conductive properties of gap-passable cells 232, each gap-passable cell 232 is affected by the applied electric field (represented by directional force arrow $F_A$) to substantially align a longitudinal axis of each gap-passable cell 232 with a field line 224 of the electric field. In one embodiment, this electric field is a non-uniform electric field such as a dielectrophoretic field in which field line 224 defines a line of maximum rate of change of a converging electric field. In other embodiments, the electric field is a generally uniform electric field.

This alignment effect caused by the electric field on the gap-passable cells causes each gap-passable cell to be rotated so that the shortest dimension of the gap-passable cell (e.g., a width) can pass through gaps 214. Meanwhile, non-passable cells 230 which do not have a dimension small enough to pass through gaps 214 are not allowed to pass through the barrier array 210, while gap-passable cells 232 are simultaneously pushed under fluid flow pressure through barrier array 210, thereby effectively separating gap-passable cells from non-passable cells.

In one embodiment, gap-passable cells 232 comprise red blood cells, which tend to be more oblate in shape, while non-passable cells 230 comprise nucleated fetal red blood cells that tend to be more spherical in shape.

Accordingly, dimension-orientation sorter 200 discriminates among differently shaped cells by using a filter structure defining an array of fluid flow openings that are sized and shaped for permitting passage of cells in which each gap-passable cell has a dimensional configuration that is capable of passing through the openings only when one or more dimensions (e.g., axes) of those appropriately shaped and sized cells are oriented by an electric field to substantially align with the dimensional configuration of the openings (e.g., gaps) in the fluid flow barriers.

Figure 4:
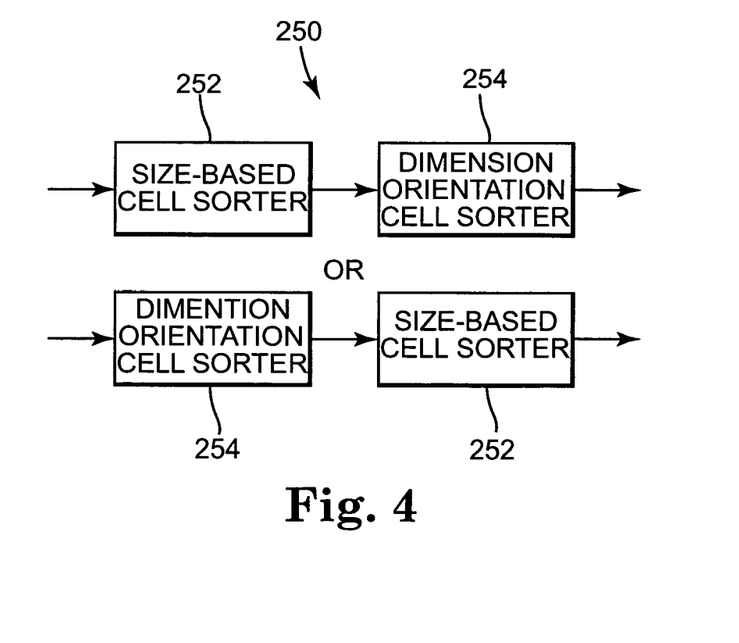
FIG. 4 is a block diagram of another cell sorter, according to an embodiment of the present invention.

FIG. 4 illustrates one embodiment of a system 250 in which a size-based cell sorter 252 and a dimension-orientation cell sorter 254 are combined in series. In one embodiment, sized-based cell sorter 252 has substantially the same features and attributes as sorter 70 of FIG. 2 while dimension-orientation cell sorter 254 has substantially the same features and attributes as sorter 200 of FIG. 3.

In one embodiment, size-based sorter 252 precedes dimension-orientation sorter 254. In this embodiment, cells are first sorted by size, via size-based sorter 252, into different groupings so that one or more groups of cells are separated from each other by size. Next, one or more groups of size-sorted cells are then sorted according to their dimensional orientation via dimension-orientation sorter 254. In particular, dimension-orientation sorter 254 permits passage of certain shape cells (e.g., oblate, prolate, etc.) having a geometrical relationship of one dimension (e.g., length) generally greater than another dimension (e.g., width) while preventing passage of other-shaped cells (e.g., spherical) that do not have a geometry that passes through the filter of dimension-orientation sorter 254.

In another embodiment, dimension-orientation sorter 254 precedes size-based sorter 252. Accordingly, cells are sorted first by orientation of one or more of their dimensions, thereby permitting passage of certain-shaped cells while excluding other shapes, as described above. Then, the certain-shaped cells or other shaped cells, are sorted by size.

Dimension-orientation sorter 254 can be implemented by one or more of dimension-orientation sorters described in association with FIGS. 5-8.

Figure 5:
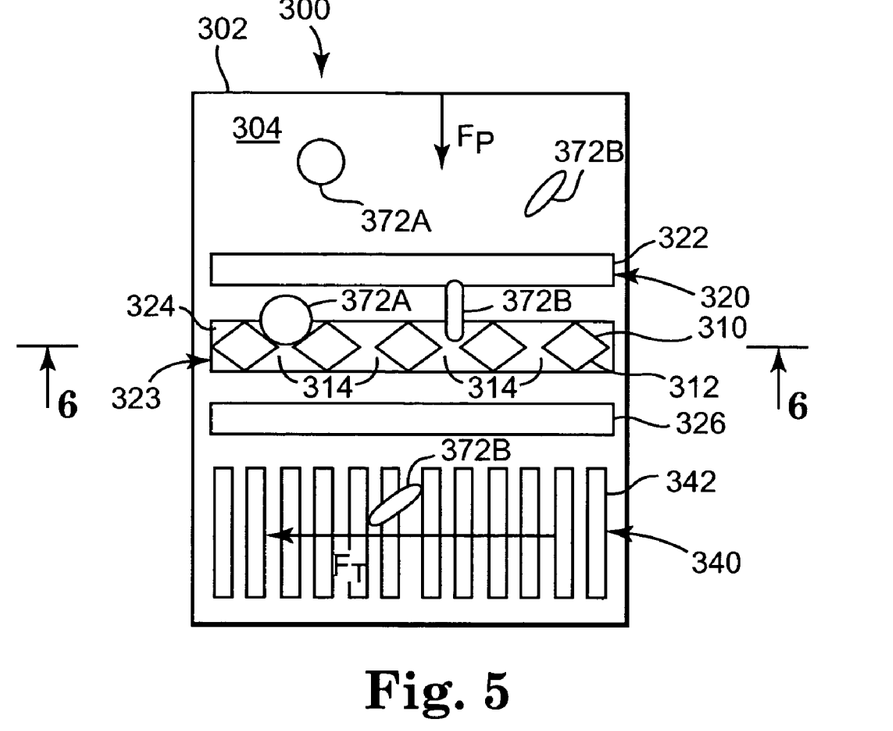
FIG. 5 is a plan view of another cell sorter, according to an embodiment of the present invention.

FIG. 5 is a top plan view of a dimension-orientation sorter 300, which is another embodiment of dimension-orientation sorter 54 of FIG. 1. As shown in the embodiment of FIG. 5, sorter 300 comprises substrate 302, surface 304, array 310 of fluid flow barriers 312 defining gaps 314, first electrode array 320 with front electrode 322 and rear electrode 326, second electrode array 323 with bottom electrode 324 and top electrode 350 (shown in FIG. 6), and electrode array 340 of electrode elements 342.

Figure 6:
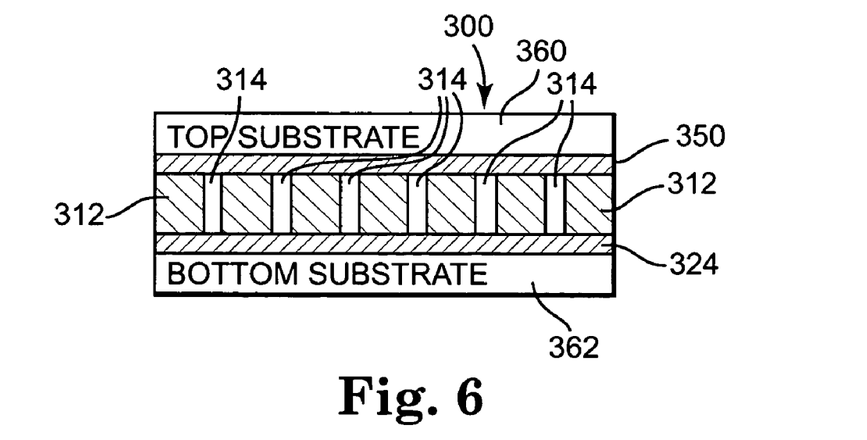
FIG. 6 is sectional view of the cell sorter of FIG. 5 as taken along lines 6-6, according to an embodiment of the present invention.

FIG. 6 is a sectional view of FIG. 5, as taken along lines 6-6. As shown in the embodiment of FIG. 6, sorter 300 further comprises top electrode 350, top substrate 360 and bottom substrate 362. FIG. 6 also further illustrates bottom electrode 324, barriers 312, gaps 314. In one embodiment, each of the elements of sorter 300 are formed within a substrate or can be individual elements formed onto or attached to a substrate.

Cells 372A, 372B move over surface 304 under fluid pressure (indicated by directional force arrow $F_P$) until they pass within the proximity of the combination of barrier array 310, first electrode array 320, and second electrode array 323, at which time gap-passable cells 372B having an appropriate geometry are permitted passage through gaps 314 while non-passable cells 372A having other shapes (e.g., spherical) are excluded from passage through gaps 314.

Front electrode 322 and rear electrode 326 of first electrode array 320 are spaced from barriers 312 (and therefore gaps 314) on opposite sides of barrier array 310 (e.g., straddling barrier array 310) to apply an electric field (such as a negative dielectrophoretic field) in which the maximum rate of change of field is aligned with gaps 314 to align cells 372B in horizontal orientation (about a vertical axis). Consequently, front electrode 322 is disposed adjacent an entrance to gaps 314 while rear electrode 326 is disposed adjacent an exit of gaps 314.

Bottom electrode 324 and top electrode 350 (FIG. 6) of second electrode array 323 are spaced from the edges of barriers 312 and apply an electric field in which a maximum rate of change of field is aligned with gaps 314 to align cells 372B in a vertical orientation (about a horizontal axis).

Accordingly, gap-passable cells 372B are oriented for passage through gaps 314 by alignment of their axes in both a horizontal and a vertical orientation via electrode arrays 320, 323. After passage through gaps 314, gap-passable cells 372B are transported in a second direction laterally away from the first direction of fluid flow, via electrode array 340, which exerts a traveling wave dielectrophoretic field on cells 372B. In one embodiment, electrode array 340 has features and attributes substantially the same as electrode arrays 140, 150, as previously described in association with FIG. 2.

Figure 7:
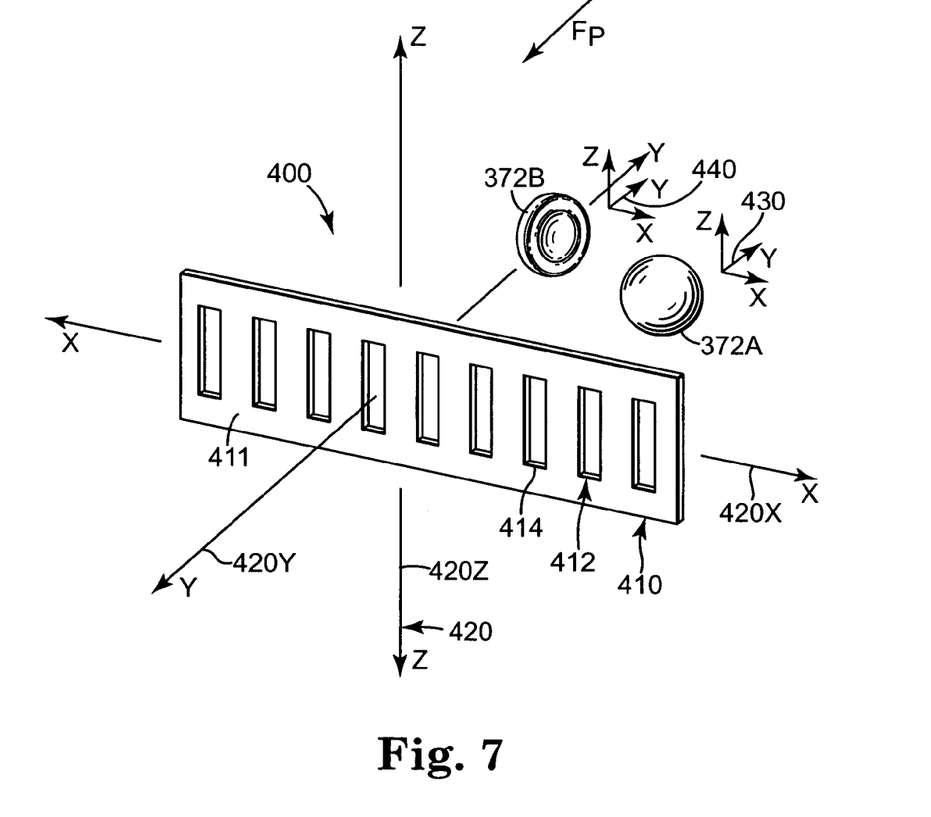
FIG. 7 is an isometric view of another cell sorter, according to an embodiment of the present invention.

FIG. 7 is an isometric view schematically illustrating a dimension-orientation sorter 400, which is another embodiment of dimension-orientation sorter 54 of FIG. 1. As shown in the embodiment of FIG. 7, sorter 400 comprises filter structure 410 for sorting cells such as non-passable cells 372A and gap-passable cells 372B (both cells 372A, B are previously described in association with FIG. 6), within a fluid flow toward filter structure 410. In this embodiment, filter structure 410 comprises plate 411 defining an array 412 of openings 414.

FIG. 7 also illustrates a three-dimensional electric field, represented by electric field array 420, that is applied about filter structure 410. Field array 420 represents electric fields that apply a force on dipole element, such as a cell, with field array 420 including force components 420X, 420Y, 420Z along one or more of three axes X, Y, and Z, respectively. In one embodiment, the electric field comprises an alignment force on cells so that cells, such as gap-passable cell(s) 372B, have their two major axes (represented by axes array 440) aligned generally parallel to y-axis 420Y and z-axis 420Z. Without this electric field applying an alignment force, cells 372B would be less likely to pass through openings 414. With or without an alignment force, non-passable cells 372A which are spherically shaped cannot pass through filter structure 410 since the dimensions of cell(s) 372A along each of three axes x, y, z of each cell 372A (represented by axis array 430) exceeds the dimensions of openings 414 in filter structure 410. Non-passable cells 372A also can be non-spherically shaped but still have one or more dimensions precluding passage of those cells through openings 414 or are cells which are not responsive the electric field.

In one embodiment, the openings 414 of filter structure are formed in a single or monolithic barrier structure, such as plate 411 with holes 414 formed in the plate, as shown in FIG. 7. In some embodiments, filter structure 410 with the array 412 of openings 414 comprises a substrate which has grooves or channels formed into the surface of the substrate to define the openings 414 of the filter structure and with the remaining portions of the substrate surface defining the barriers in the fluid flow. In other embodiments, filter structure 410 comprises an array of individual barriers disposed on a surface to define openings 414 between the respective barriers. Accordingly, filter structure 410 can be implemented as a single structure, or a combination of structures, that define an arrangement of passages and barriers to direct fluid flow and cells through the passages, as permitted by the size and geometry of the passages relative to the cells, as well as by the alignment forces on the cells applied by the electric field array 420.

Finally, the electric field array 420 can be applied by a number of different electrode arrangements. In one embodiment, the electrode arrangement is substantially similar to that shown in FIG. 6 in which electrode elements are placed in the front and rear, and top and bottom positions relative to filter structure 410 in a manner that permits fluid flow of cells about, over or through the electrode elements. In other embodiments, the electrode arrangement can be a grid of electrode elements, an electric screen, other arrangement of electrode elements disposed to apply the electric field about filter structure, so long as the electrode elements still permit the intended fluid flow path relative to the filter structure 410.

In use, cells 372A, 372B move under fluid pressure (indicated by directional force arrow $F_P$) toward sorter 400 until they pass within the proximity of sorter 400, at which time gap-passable cells 372B having an appropriate geometry (e.g., prolate, oblate, cylindrical, etc) are permitted passage through openings 414 while non-passable cells 372A having other dimensional configurations (e.g., spherical) are excluded from passages through sorter 400. Gap-passable cells 372B have one dimension (e.g., along z axis or y-axis of cell 372B) that would otherwise prevent passage through openings 414, but have other dimensions (e.g., along z-axis of cell 372B) that are small enough to pass through openings 414. Cells 372B are therefore permitted passage through sorter 400 while cells 372A are excluded because gap-passable cell(s) 372B become oriented via the electric field array 420 (applied primarily along z-axis 420Z and y-axis 420Y) with their smallest dimension in alignment with the smallest dimension of openings 414, and oriented with their largest dimensions in alignment with the largest dimension of openings 414.

Accordingly, in dimension-orientation sorter 400, cells 372B are aligned both vertically and horizontally to pass through openings 422. In some embodiments, after passage through openings 414 of arrays 412, gap-passable cells 372B may be transported away via a traveling wave dielectrophoretic field on cells 372B, in substantially the same manner as described in association with FIG. 6.

Figure 8:
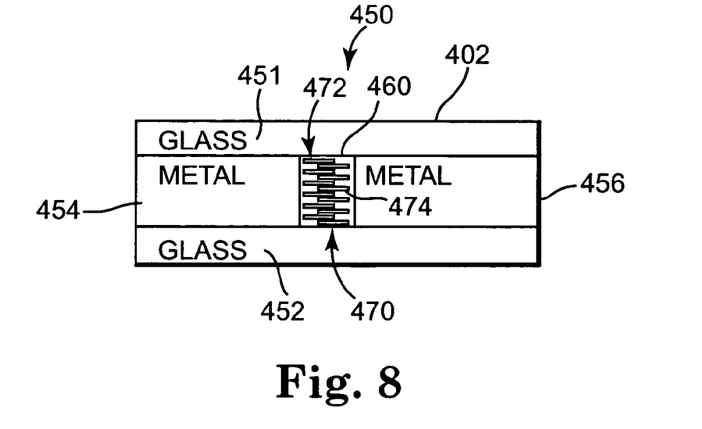
FIG. 8 is sectional view of another cell sorter, according to an embodiment of the present invention.

FIG. 8 illustrates dimension-orientation sorter 450 which is another embodiment of dimension-orientation sorter 54 of FIG. 1. In one embodiment, sorter 450 comprises upper glass substrate 451, lower glass substrate 452, and metal electrodes 454 and 456, which together define passageway 460. Sorter 450 also includes filter plate 470 which defines an array 472 of elongate openings 474. Metal electrodes 454 and 456 are sandwiched between upper and lower glass substrates 451, 452. In one embodiment, the metal electrodes 454, 456 are formed and then the glass substrates 451, 452 are anodically or adhesively bonded to the metal electrodes. After polishing a surface of the assembly, filter plate 470 is attached to metal electrodes 454, 456 to place array 472 within passageway 460, thereby providing a field-enhanced filter with gaps 474 for discriminating shaped cells via alignment of the cells by an electric field applied by metal electrodes 454, 456.

It is understood that any one or more of dimension-orientation sorters 200, 300, 400, 450 can be implemented as dimension-orientation sorter 54 of FIG. 1 or dimension-orientation sorter 254 of FIG. 4.

Embodiments of the present invention enable sorting of cells based on at least one of a size and a dimensional orientation of the cells by combining one or more array(s) of fluid barriers with an electric field to accentuate directed passage of differently-sized and/or differently-shaped cells through the cell sorter.

Although specific embodiments have been illustrated and described herein, it will be appreciated by those of ordinary skill in the art that a variety of alternate and/or equivalent implementations may be substituted for the specific embodiments shown and described without departing from the scope of the present invention. This application is intended to cover any adaptations or variations of the specific embodiments discussed herein. Therefore, it is intended that this invention be limited only by the claims and the equivalents thereof.

What is claimed is:

1. A micro-filtration device for sorting cells comprising:
an apparatus including a barrier structure defining an array of openings arranged within a fluid flow path, the openings having at least one of a size and a shape configured to direct only a portion of the cells through the openings based on at least one of a size and a shape of each cell; and
an electrode arrangement disposed about the array of openings and configured to apply non-uniform electric field to enhance passage of the portion of the cells through the openings, wherein the electrode arrangement is separate from, and independent of, the barrier structure.

2. The device of claim 1, wherein the fluid flow path is configured to conduct cells in a first direction to move the cells through the apparatus, and wherein the electrode arrangement is arranged to generate the non-uniform electric field as a temporally varying non-uniform electric field to move the portion of the cells, after passage through the barrier structure, in a second direction generally transverse to the first direction.

3. The device of claim 1, wherein the openings have an elongate shape and the electrode arrangement is arranged to apply the non-uniform electric field in substantial alignment with the elongate shape of the openings.

4. A micro-filtration device for sorting cells comprising:
an apparatus including a barrier structure defining an array of openings arranged within a fluid flow path, the openings having at least one of a size and a shape configured to direct only a portion of the cells through the openings based on at least one of a size and a shape of each cell, wherein the fluid flow path is configured to conduct cells in a first direction to move the cells through the apparatus; and
an electrode arrangement disposed about the array of openings and configured to apply a non-uniform electric field to enhance direction of the portion of the cells through the openings, wherein the electrode arrangement is arranged to generate the non-uniform electric field as a temporally varying non-uniform electric field in a second direction different from the first direction;
wherein the openings include:
a first set of openings permitting passage of cells of a first size in the first direction;
a second set of openings permitting passage of cells of a second size, smaller than the first size, in the first direction; and
a third opening extending transversely between the first and second set of openings, and permitting movement of cells of the first size in the second direction; and
wherein the electrode arrangement includes a first electrode array extending within the third opening and configured to apply the temporally varying non-uniform electric field to move cells of the first size in the second direction, which is transverse to the first direction of the fluid flow path, away from the first and second set of openings.

5. A micro-filtration device for sorting cells comprising:
an apparatus including a barrier structure defining an array of openings arranged within a fluid flow path, the openings having at least one of a size and a shape configured to direct only a portion of the cells through the openings based on at least one of a size and a shape of each cell, wherein the fluid flow path is configured to conduct cells in a first direction to move the cells through the apparatus; and
an electrode arrangement disposed about the array of openings and configured to apply a non-uniform electric field to enhance direction of the portion of the cells through the openings, wherein the electrode arrangement is arranged to generate the non-uniform electric field as a temporally varying non-uniform electric field in a second direction different from the first direction;
wherein the barrier structure comprises:
a plurality of barrier arrays aligned generally parallel to each other to define a succession of barrier arrays, each successive barrier array defining a smaller set of passages to progressively sort cells in decreasing size into different respective portions as the cells move in the fluid flow path in the first direction; and
a plurality of transport paths disposed between and extending transversely to the successive barrier arrays with each transport path including one of a plurality of electrode arrays of the electrode arrangement, each respective electrode array configured to apply the temporally varying non-uniform electric field to move the respective portion of the cells through each respective transport path in the second direction.

6. A micro-filtration device for sorting cells comprising:
an apparatus including a barrier structure defining an array of openings arranged within a fluid flow path, the openings having at least one of a size and a shape configured to direct only a portion of the cells through the openings based on at least one of a size and a shape of each cell, wherein the openings have an elongate shape; and
an electrode arrangement disposed about the array of openings and configured to apply a non-uniform electric field to enhance direction of the portion of the cells through the openings, wherein the electrode arrangement is arranged to apply the non-uniform electric field in substantial alignment with the elongate shape of the openings;

and wherein the array of openings comprises:

a first set of openings wherein the electrode arrangement straddles the first set of openings to apply the non-uniform electric field to substantially align a long axis of the cells with a long axis of the openings of the first set of openings.

7. The device of claim 6, wherein the electrode arrangement comprises:

a first pair of electrodes including a first electrode and a second electrode, the first electrode and the second electrode disposed on opposite sides of the first set of openings and configured to apply the non-uniform electric field.

8. The device of claim 7, wherein the first electrode is disposed above the first set of openings and the second electrode is disposed below the first set of openings to apply the non-uniform electric field as a first non-uniform electric field.

9. The device of claim 7, wherein the first electrode is disposed at an entrance of the first set of openings and the second electrode is disposed at an exit of the first set of openings to apply the non-uniform electric field as a second non-uniform electric field.

10. The device of claim 7, wherein the first electrode is disposed above the first set of openings and the second electrode is disposed below the first set of openings to apply the non-uniform electric field as a first non-uniform electric field; and wherein the electrode arrangement further comprises:

a second pair of electrodes with a first electrode and a second electrode, wherein the first electrode of the second pair of electrodes is disposed adjacent an entrance of the first set of openings and the second electrode of the second pair of electrodes is disposed adjacent an exit of the first set of openings to apply the non-uniform electric field as a second non-uniform electric field.

11. A micro-filtration device for sorting cells comprising:

an apparatus including a barrier structure defining an array of openings arranged within a fluid flow path, the openings having at least one of a size and a shape configured to direct only a portion of the cells through the openings based on at least one of a size and a shape of each cell;

an electrode arrangement disposed about the array of openings and configured to apply an electric field to enhance direction of the portion of the cells through the openings; and at least one of an acoustic device and an electric device with each respective device configured to apply a force to the cells traveling along the fluid flow path to prevent aggregation of the cells within the apparatus.

12. A cell sorter chip comprising:

means for sorting cells based on a plurality of dimensions of the cells; and means for electrically enhancing the sorting of cells, wherein the means for sorting and the means for electrically enhancing the sorting together comprise at least one of:

a first filtration device that sorts cells according to their sizes, wherein the first filtration device is succeeded within a fluid flow path by a second filtration device that sorts cells according to their dimensional orientation; or a third filtration device that sorts cells according to their dimensional orientation, wherein the third filtration device is succeeded within the fluid flow path by a fourth filtration device that sorts cells according to their sizes.

13. The chip of claim 12, wherein each of the respective first, second, third and fourth filtration devices comprises:

a barrier structure defining openings.

14. The chip of claim 13, wherein the means for electrically enhancing the sorting comprises an electrode array disposed and arranged to convey the cells away from the respective first, second, third, and fourth filtration devices.

15. The chip of claim 12, wherein the means for electrically enhancing the sorting comprises:

a first electrode arrangement configured to apply a temporally varying non-uniform electric field in at least one of the first filtration device or the fourth filtration device to move groups of cells, sorted according to their respective sizes, out of the at least one of the first filtration device or the fourth filtration device, respectively; and a second electrode arrangement configured to apply an electric field in at least one of the second filtration device or the third filtration device to permit cell passage within the at least one of the second filtration device or the third filtration device, respectively, by causing at least one dimension of the cells to become aligned with a gap that has a shape and a size substantially matching the at least one dimension of the cells.

16. A cell sorter chip comprising:

means for sorting cells based on a plurality of dimensions of the cells, the means for sorting including a substrate having a barrier structure defining openings, wherein the openings each have a long axis; and means for electrically enhancing the sorting of cells, including an electrode array disposed and arranged to generate an electric field to align a long axis of the cells with the long axis of the openings.

17. The chip of claim 16 wherein the electric field is a non-uniform electric field.

18. A cell sorter chip comprising:

means for sorting cells based on a plurality of dimensions of the cells, including a substrate having a barrier structure defining openings;

means for inducing a fluid flow on the substrate in a first direction along a path of the fluid flow through the openings; and means for electrically enhancing the sorting of cells via transporting the cells in a second direction to a location out of the fluid flow.

19. The chip of claim 18, wherein the means for electrically enhancing the sorting comprises an electrode array disposed and arranged to apply a temporally varying non-uniform electric field to transport a certain size range of cells out of the fluid flow.

20. A method of sorting cells on a biodevice comprising:

directing a flow of cells within a fluid into a filtration structure defining an array of fluid openings; and encouraging cell passage of each cell of a portion of the cells through the fluid openings based on at least one dimension of each cell via application of a non-uniform electric field within the fluid openings.

21. The method of claim 20, wherein encouraging cell passage comprises:

aligning each cell in the portion of the cells relative to the fluid openings.

22. A method of sorting cells on a biodevice comprising:
directing a flow of cells within a fluid into a filtration structure defining an array of fluid openings, wherein the fluid openings include an elongate shape, each fluid opening has a major axis substantially perpendicular to a direction of fluid flow through the fluid openings, and each cell has at least one major axis; and
encouraging cell passage of each cell of a portion of the cells through the fluid openings based on at least one dimension of each cell via application of an electric field within the fluid openings to align the at least one major axis of each cell with the major axis of one of the fluid openings.

23. The method of claim 22, wherein the at least one major axis includes two major axes and each cell has the two major axes and a minor axis.

24. The method of claim 22, wherein the at least one major axis of each cell defines one major axis and wherein encouraging cell passage comprises aligning the one major axis of each cell with a direction of passage through the fluid openings.

25. A method of sorting cells on a biodevice comprising:
directing a flow of cells within a fluid into a filtration structure defining successive arrays of fluid openings;
separating the cells as the cells flow through the successive arrays of fluid openings with each successive array of fluid openings having decreasing dimensions to sort the cells into different groups based on their size;
encouraging cell passage of each cell of a portion of the cells through the respective fluid openings based on at least one dimension of each cell via application of a first non-uniform electric field within the fluid openings; and
moving the different groups of cells in independent, generally parallel pathways in a direction generally transverse to the flow of cells through the array of fluid openings by application of a temporally varying second non-uniform electric field along each respective pathway.

* * * * *

UNITED STATES PATENT AND TRADEMARK OFFICE
CERTIFICATE OF CORRECTION

PATENT NO. : 7,390,388 B2 Page 1 of 1
APPLICATION NO. : 10/808945
DATED : June 24, 2008
INVENTOR(S) : Winthrop D. Childers et al.

It is certified that error appears in the above-identified patent and that said Letters Patent is hereby corrected as shown below:

In column 13, line 47, in Claim 1, after "apply" insert -- a --.

Signed and Sealed this

Eighteenth Day of November, 2008

JON W. DUDAS
*Director of the United States Patent and Trademark Office*